United States Patent [19]
Garcia et al.

[11] 4,087,425
[45] May 2, 1978

[54] N,N-DISULFONYLPIPERAZINES

[75] Inventors: Antonio Alcaide Garcia, Guadalajara; Juan Ramon Conde Ruiz; Juan Bermejo Lozano, both of Madrid, all of Spain

[73] Assignee: Laboratorios Liade, S.A., Madrid, Spain

[21] Appl. No.: 713,639

[22] Filed: Aug. 12, 1976

[51] Int. Cl.$^2$ ............................................. C07D 295/18
[52] U.S. Cl. ...................................... 544/383; 424/250
[58] Field of Search ...................................... 260/268 S

[56]      References Cited
        U.S. PATENT DOCUMENTS 3,943,135  3/1976  Fujii ................................ 260/268 S Primary Examiner—Jose Tovar

[57]        ABSTRACT

This invention is directed to a novel series of piperazine derivatives having the general structure

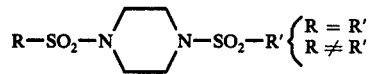

wherein R and R' may be:

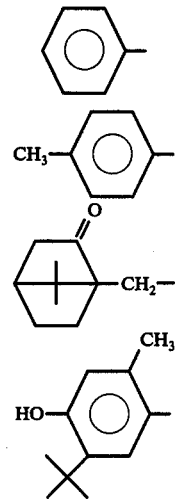

9 Claims, No Drawings

N,N-DISULFONYLPIPERAZINES

This invention is directed to a novel series of piperazine derivatives having the general structure

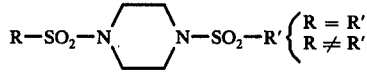
$\begin{cases} R = R' \\ R \neq R' \end{cases}$ wherein R and R' may be:

R,R'

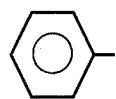

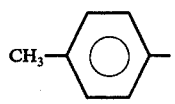

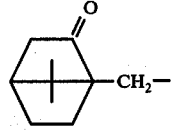

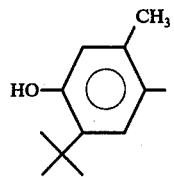

These compounds have shown a strong central analgesic action after being administered orally.

A cardiac stimulating action has been detected, this action being depressing in some cases.

A spasmolitic action on the smooth muscle is also observed.

Besides these properties, an important local anesthetic action and a remarkable anticholinergic activity have been noted.

Finally, the acute toxicity is very low, the active doses being far-away from the toxic doses.

DESCRIPTION OF THE PROCESS

The compounds are synthetized following a one-step method, by reacting piperazine or monosulfonylpiperazine with the corresponding sulfonyl chloride in ethanol/NaOH (Method A) or in DMF/Et₃N (Method B):

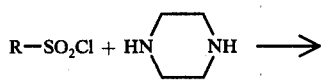

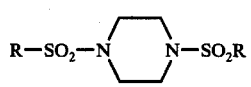

being R = R'

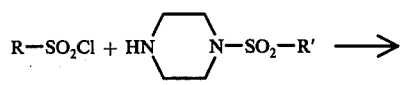

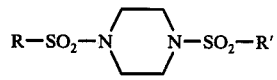

being R ≠ R'.

GENERAL METHOD (A) When R = R'

0.01 Mol of piperazine are dissolved in aqueous etharol. 0.02 M of sulfonyl chloride are added in ethanol. The reaction mixture is cooled in a ice-beth and stirred for 1 hour. The precipitate is filtered, washed with H₂O, dried, and crystallized from nitrobenzene or ethanol.

When R ≠ R'

The same general method is followed, the relative amounts of reactants being different:

0.01 Mol of monosulfonylpiperazine, 0.01 Mol of NaOH and 0.01 Mol of sulfonyl chloride.

(B) When R = R'

0.01 Mol of piperazine and 0.02 Mol of Et₃N are dissolved in DMF. 0.02 Mol of sulfonylchloride are added, cooling in an ice-bath and stirring for 1 hour. The precipitate of triethylamine hidrochloride is filtered off, and the DMF solution is added on destilled water. The compound precipitates. It is filtered, washed with water and crystallized from aqueous ethanol.

When R ≠ R'

The same general method is aplied, changing the relative amounts of reactants:

0.01 Mol of piperazine, 0.01 Mol Et₃N and 0.01 Mol of sulfonylchloride.

EXAMPLE 1

N, N' di-p-toluensulfonylpiperazine

Method A
Yield: 87%
Crystallized from nitrobenzene
M.P. = 298° (d)

EXAMPLE 2

N,N'-dicamphorsulfonyl-piperazine

Method A
Yield: 80%
Crystallized from nitrobenzene
M.P = 280 (d)

EXAMPLE 3

N-p-toluensulfonyl, N'-camphorsulfonylpiperazine

Method A
Yield: 55%
Crystallized from ethanol
M.P 190°–192° C

EXAMPLE 4

N.N' debenzene-sulfonylpiperazine

Method A
Yield: 70%
Crystallized from nitrobenzene
M.P. = 280°–282° C

EXAMPLE 5

N-benzenesulfonyl,N'-p-toluensulfonylpiperazine

Method A

Yield: 60%
Crystallized from nitrobenzene
M.P. = 257°–258° C

EXAMPLE 6

N-benzenesulfonil,N'-camphorsulfonylpiperazine

Method A
Yield: 53%
Crystallized from ethanol
M.P. = 178°–180°C

EXAMPLE 7

N-p-toluensulfonil,N'-Thymolsulfonylpiperazine

Method B
Yield: 62%
Crystallized from ethanol
M.P. = 216°–218° C

EXAMPLE 8

N,N'-dithymolsulfonylpiperazine

Method B
Yield: 67%
Crystallized from ethanol/water
M.P. = 285°–288° C

EXAMPLE 9

N-benzenesulfonyl,N'-thymolsulfonylpiperazine

Method B
Yield 60%
Crystallized from ethanol/water
M.P. = 162°–164° C

What we claim is:

1. A piperazine derivative having the general structure

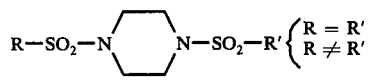

wherein R and R' are selected from the group consisting of

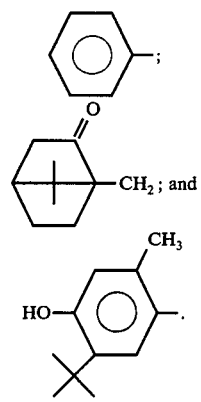

2. The compound as claimed in claim 1 having the formula N,N'-dicamphorsulfonylpiperazine.

3. The compound as claimed in claim 1 having the formula N-p-toluensulfonyl, N'-camphorsulfonylpiperazine.

4. The compound as claimed in claim 1 having the formula N,N' debenzene-sulfonylpiperazine.

5. The compound as claimed in claim 1 having the formula N-benzenesulfonyl, N'-p-toluensulfonylpiperazine.

6. The compound as claimed in claim 1 having the formula N-benzenesulfonil, N'-camphorsulfonylpiperazine.

7. The compound as claimed in claim 1 having the formula N-p-toluensulfonil, N'-Thymolsulfonylpiperazine.

8. The compound as claimed in claim 1 having the formula N,N'-dithymolsulfonylpiperazine.

9. The compound as claimed in claim 1 having the formula N-benzenesulfonyl, N'-thymolsulfonylpiperazine.

* * * * *